United States Patent
Yi et al.

(10) Patent No.: US 7,669,337 B2
(45) Date of Patent: Mar. 2, 2010

(54) SAFETY SCALPEL

(75) Inventors: Patrick Yi, Singapore (SG); Kook-Ting Foo, Singapore (SG); Poh-Hock Neo, Singapore (SG)

(73) Assignee: MediPurpose Pte. Ltd., Singapore (SG)

( * ) Notice: Subject to any disclaimer, the term of this patent is extended or adjusted under 35 U.S.C. 154(b) by 817 days.

(21) Appl. No.: 11/259,939

(22) Filed: Oct. 26, 2005

(65) Prior Publication Data
US 2006/0095057 A1 May 4, 2006

Related U.S. Application Data

(60) Provisional application No. 60/623,741, filed on Oct. 29, 2004.

(51) Int. Cl.
*A61B 17/32* (2006.01)
(52) U.S. Cl. .............. 30/155; 30/162; 30/339; 606/167
(58) Field of Classification Search ......... 606/167; 30/155, 162, 339
See application file for complete search history.

(56) References Cited

U.S. PATENT DOCUMENTS

| | | | |
|---|---|---|---|
| 5,299,357 A | | 4/1994 | Wonderley et al. |
| 5,330,493 A | * | 7/1994 | Haining ............ 606/167 |
| 5,342,379 A | | 8/1994 | Volinsky |
| 5,741,289 A | | 4/1998 | Jolly et al. |
| 5,868,771 A | * | 2/1999 | Herbert et al. .......... 606/167 |
| 5,924,206 A | * | 7/1999 | Cote et al. ................ 30/337 |
| 5,941,892 A | * | 8/1999 | Cohn et al. ............. 606/167 |
| 6,022,364 A | | 2/2000 | Flumene et al. |
| 6,053,929 A | * | 4/2000 | Cohn et al. ............. 606/167 |
| 6,254,621 B1 | | 7/2001 | Shackelford et al. |
| 6,589,258 B2 | | 7/2003 | Pilo et al. |
| 6,757,977 B2 | | 7/2004 | Dambal et al. |
| 6,884,240 B1 | * | 4/2005 | Dykes ....................... 606/1 |
| 7,172,611 B2 | * | 2/2007 | Harding et al. ......... 606/167 |

FOREIGN PATENT DOCUMENTS

| | | |
|---|---|---|
| EP | 0958788 | 11/1999 |
| EP | 1031322 | 8/2000 |

OTHER PUBLICATIONS

The International Search Report for PCT/US2005/038588.

\* cited by examiner

*Primary Examiner*—Kenneth E. Peterson
(74) *Attorney, Agent, or Firm*—Troutman Sanders LLP; Ryan A. Schneider; Filip A. Kowalewski

(57) ABSTRACT

A safety scalpel that incorporates a reusable metal scalpel handle similar in shape and feel to the conventional metal handle preferred by most surgeons, and a disposable blade cartridge that covers the blade before, during and after use, and is easily mounted and released from the scalpel handle. The blade cartridge includes a blade with similar cutting profiles as standard surgical blades, a blade holder that is permanently fixed to the blade, and a blade guard that covers the blade and within which the blade holder is able to slide. The scalpel handle is reusable, while the blade cartridge is disposable. The blade cartridge is attached to and detached from the scalpel handle in a direction generally perpendicular the longitudinal axis of the scalpel handle.

18 Claims, 10 Drawing Sheets

SAFETY SCALPEL

CROSS REFERENCE TO RELATED APPLICATION AND CLAIM OF BENEFIT

This application claims the benefit of U.S. Provisional Application 60/623,741 filed on Oct. 29, 2004.

FIELD OF THE INVENTION

The present invention relates generally to scalpel devices and, in particular, to safety scalpels for medical use.

BACKGROUND OF THE INVENTION

Health care is the second fastest growing sector of the U.S. economy, employing over 12 million workers. Women represent nearly 80% of the health care work force. Health care workers face a wide range of hazards on the job, including needlestick and sharps injuries, back injuries, latex allergies, violence, and stress. Although it is possible to prevent or reduce health care worker exposure to these hazards, health care workers are actually experiencing increasing numbers of occupational injuries and illnesses. Rates of occupational injury to health care workers have risen over the past decade. By contrast, two of the most hazardous industries, agriculture and construction, are safer today than they were a decade ago.

Precise national data is not available on the annual number of needlestick and other percutaneous injuries among health care workers; however, estimates indicate that 600,000 to 800,000 such injuries occur annually. About half of these injuries go unreported. Data from EPINet (the Exposure Prevention Information Network) suggests that at an average hospital, workers incur approximately thirty needlestick injuries per 100 beds per year.

Most reported needlestick and sharps injuries involve nursing staff; but laboratory staff, physicians, housekeepers, and other health care workers are also injured. Some of these injuries expose workers to bloodborne pathogens that can cause infection. The more serious of these pathogens are the hepatitis B virus (HBV), the hepatitis C virus (HCV), and the human immunodeficiency virus (HIV). Infections by each of these pathogens are potentially life threatening, yet preventable.

The emotional impact of needlestick and sharp injuries can be severe and long lasting, even when a serious infection is not transmitted. This impact is particularly severe when the injury involves exposure to HIV. In one study of twenty health care workers with an HIV exposure, eleven reported acute severe distress, seven had persistent moderate distress, and six quit their jobs as a result of the exposure. Other stress reactions requiring counseling have also been reported. Not knowing the infection status of the source patient can accentuate the health care worker's stress. In addition to the exposed health care worker, colleagues and family members may suffer emotionally.

Safety and health issues can best be addressed in the setting of a comprehensive prevention program that considers all aspects of the work environment and that has employee involvement as well as management commitment. Implementing the use of improved engineering controls is one component of such a comprehensive program. Other prevention strategy factors that must be addressed, however, include modification of hazardous work practices, administrative changes to address needle hazards in the environment (e.g., prompt removal of filled sharps disposal boxes), safety education and awareness, feedback on safety improvements, and action taken on continuing problems.

Improved engineering controls are often among the most effective approaches to reducing occupational hazards and, therefore, are an important element of a needlestick prevention program. Such controls include eliminating the unnecessary use of needles and implementing devices having safety features. A number of sources have identified several desirable characteristics for safety devices, which include preferences for safety devices that: do not use needles; incorporate the safety feature as an integral part of the device; work passively (i.e., requires no activation by the user); have a safety feature that can be engaged with a single-hand technique and allows the worker's hands to remain behind the exposed sharp, if user activation is necessary; allow the user to easily determine whether the safety feature is activated; have a safety feature that cannot be deactivated and remains protective through disposal; perform reliably; are easy to use and practical; and are safe and effective for patient care.

Although each of these characteristics is desirable, some are not feasible, applicable, or available for certain health care situations. For example, needles will always be necessary where alternatives for skin penetration are not available. Also, a safety feature that requires activation by the user might be preferable to one that is passive in some cases. Each device must be considered on its own merit and ultimately on its ability to reduce workplace injuries.

Regarding specifically scalpels, the conventional scalpel currently used in the healthcare industry includes a metal handle and a disposable blade that is mounted on the handle prior to use, and removed after use. The process of mounting and dismounting of the blade is a difficult and dangerous procedure, which exposes the medical practitioner to potential injury from the exposed blade and contamination due to blood that may be present on the blade. Further, sharps injuries may also occur during an operation as the surgeon passes the exposed scalpel to a colleague.

Current safety scalpels have been designed around the concept of a retracting guard or retracting blade on a plastic handle, where the entire scalpel is disposable. Because the entire scalpel is disposable, there is no need to mount and dismount the blade. The guard covers the blade before, during, and after use, and therefore protects the user from sharps injury.

Surgeons who have developed a feel for the shape and weight of the metal handle dislike the current disposable safety scalpels as, among other things, the plastic handle is too light and feels "different." During use, the plastic handle of the scalpel incurs undesirable flexibility than that of a metal handle scalpel. In addition, the disposable safety scalpel is significantly more expensive than the regular disposable blade. These two factors currently limit the adoption of safety scalpels in the healthcare industry.

What is needed is a safe and reliable scalpel that overcomes the present objections from the healthcare practitioner of current designs, while providing adequate protection for the medical workers handling the scalpel. It is to such a device that the present invention is primarily directed.

SUMMARY OF THE INVENTION

Briefly described, in a preferred form, the present invention is an improvement over the conventional scalpel by providing a safety scalpel that incorporates a reusable metal scalpel handle similar in shape and feel to the conventional metal handle preferred by most surgeons, and a disposable blade cartridge that covers the blade before, during, and after use, and is easily mounted and released from the metal scalpel handle.

The present safety scalpel comprises a blade with similar cutting profiles as standard surgical blades, a blade holder that is permanently fixed to the blade, a blade guard that covers the blade and within which the blade holder is able to slide, a scalpel handle that receives a blade cartridge (being the blade, blade holder and blade guard assembled together), and a lock. The scalpel handle is reusable, while the blade cartridge is disposable.

While prior art designs have incorporated disposable blade cartridges where the blade guard slides off the releaseably fixed blade, the present invention is based on the blade sliding out of the releaseably fixed guard.

The present invention comprises a safety disposable blade cartridge that can be used with either a preferably reusable metal, or disposable plastic, scalpel handle. The blade cartridge easily fixes onto the scalpel handle, and yet is securely locked on the scalpel handle. The blade is preferably movable through at least three distinct positions—open, closed, and locked.

Attaching and detaching the blade cartridge to the scalpel handle utilizes a lateral approach generally perpendicular to a longitudinal axis of the scalpel handle. When fixed to the scalpel handle, only the blade and blade holder of the blade cartridge can move in a longitudinal direction, as the blade guard experiences limited or no longitudinal movement.

In other embodiments, the blade cartridge is itself a standalone mini-scalpel, which is securely fixed to a passive metal handle, or the blade can move within a hollow metal handle.

BRIEF DESCRIPTION OF THE DRAWINGS

FIG. 13B illustrates an alternative embodiment wherein a boss of the blade holder engages the blade guard to prevent the blade from lateral and transverse movement.

DETAILED DESCRIPTION OF A PREFERRED EMBODIMENT

Figure 1:
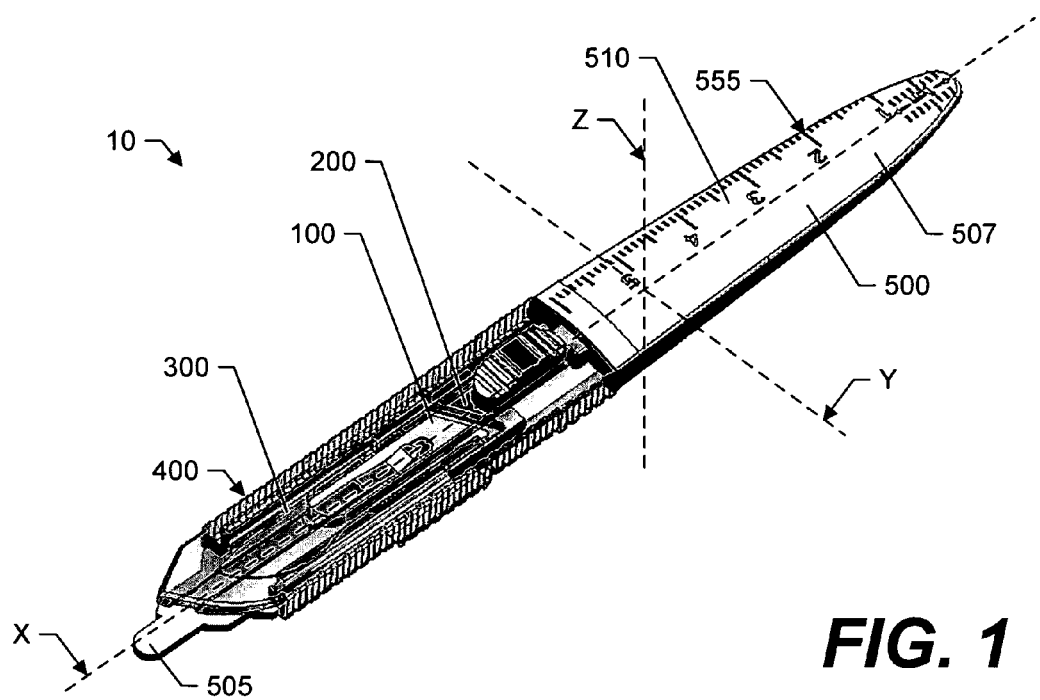
FIG. 1 illustrates a perspective view of a blade cartridge and passive scalpel handle in accordance with preferred embodiments of the present invention.

Referring now in detail to the figures, wherein like reference numerals represent like parts throughout the several views, the present safety scalpel 10 of FIG. 1 comprises a scalpel handle 500 and a blade cartridge 400, such that the blade cartridge 400 is configured for secure attachment to and safe detachment from the scalpel handle 500. In a preferred embodiment of the present invention, the blade cartridge 400 is disposable, while the scalpel handle 500 is non-disposable. Accordingly, a new blade cartridge 400 can be attached to the scalpel handle 500 for use by, for example, a medical practitioner. After the medical practitioner has finished using the safety scalpel 10, the blade cartridge 400 can be safely removed from the scalpel handle 500, so that the blade cartridge 400 can be disposed of properly.

For purposes of describing directional relationship of the various components of the safety scalpel 10, the safety scalpel 10 includes a longitudinal axis X extending along the length of the safety scalpel 10, a lateral axis Y that extends generally perpendicular to the longitudinal axis X along the width of the safety scalpel 10, and a transverse axis Z that extends generally perpendicular to the longitudinal axis X and the lateral axis Y along the height of the safety scalpel 10. Accordingly, as used herein, longitudinal movement refers to movement along the longitudinal axis X, lateral movement refers to movement along the lateral axis Y, and transverse movement refers to movement along the transverse axis Z.

The blade cartridge 400 can comprise a blade 100, a blade holder 200 adapted to securely engage the blade 100, and a blade guard 300 configured to slideably receive the blade 100 and blade holder 200. Further, the blade holder 200 is adapted to move the blade 100, or a portion thereof, between a closed and open position. In the closed position, the blade 100 is safely and fully contained within the blade guard 300. In the open position, the blade 100, or a portion thereof, extends outside the blade guard 300. As designed, the blade 100 is in the closed position during non-use of the safety scalpel 10 and in the open position during active use of the safety scalpel 10. The safety scalpel 10 of the present invention, therefore, provides a safe and effective tool.

Figure 2:
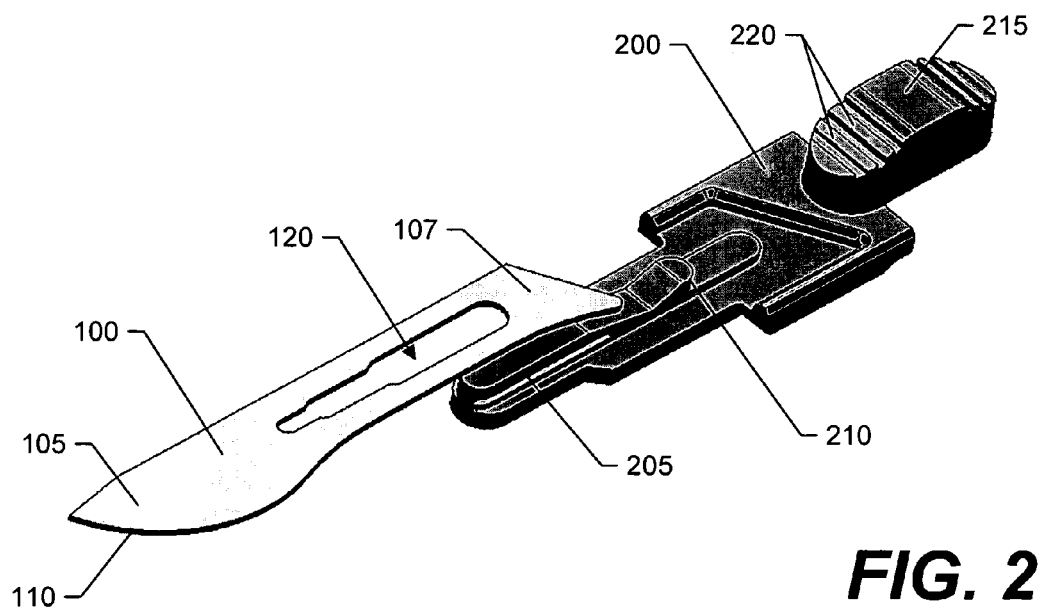
FIG. 2 illustrates a perspective view of a blade and a blade holder, wherein the blade is detached from the blade holder, in accordance with preferred embodiments of the present invention.
Figure 3:
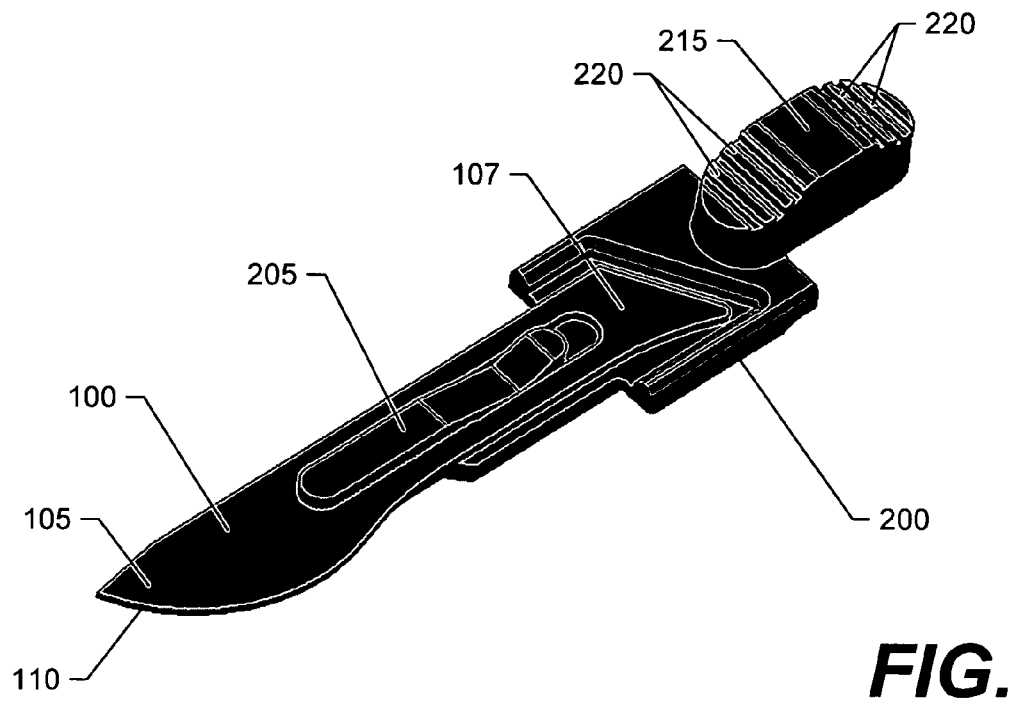
FIG. 3 illustrates a perspective view of the blade and blade holder, wherein the blade is securely attached to the blade holder, in accordance with preferred embodiments of the present invention.

As illustrated in FIGS. 2 and 3, the blade 100 includes a cutting edge 110 located at a distal end 105 of the blade 100. Further, at a proximal end 107, the blade 100 defines an aperture 120; preferably an elongated aperture 120 such as a slot. Other than perhaps the profile of the cutting edge 110, the blade 100 has a similar front and back face.

One skilled in the art will recognize that the blade 100 can be made of a variety of suitable materials including, but not limited to, both carbon and stainless steel. Generally, the carbon and stainless steel used to create the blade 100 are manufactured in compliance with several industry standards including British Standard ("BS") 2982:1992, International Organization for Standardization ("ISO") 7740:1985 and European Standard ("EN") 27740:1992. The blade 100 further can be sterilized by, for example, gamma radiation.

As illustrated in FIG. 2, blade holder 200 is designed to mate with blade 100. Unlike the blade 100, the front and back face of the blade holder 200 are dissimilar, and the thickness of the blade holder 200 is non-uniform. A distal end of blade holder 200 comprises a holder protrusion 205 extending vertically from the front face of the blade holder 200, in a profile that generally corresponds to the aperture 120 of the blade 100. The holder protrusion 205 is adapted to securely engage the aperture 120 of the blade 100.

The blade holder 200 can further comprise a protrusion notch 210 located on a proximal side of the holder protrusion 205, such that the protrusion notch 210 locks the blade 100 to the blade holder 200. As the holder protrusion 205 passes through the blade aperture 120, the blade 100 snaps into the protrusion notch 210, thereby preventing the blade 100 from disengaging with the blade holder 200.

During assembly of the blade cartridge 400, the blade 100 is fixed to the blade holder 200 by aligning the aperture 120 of the blade 100 with the corresponding holder protrusion 205 of the blade holder 200. The holder protrusion 205 and the protrusion notch 210 allow the blade 100 to slide, slot, and snap onto the blade holder 200, as shown in FIGS. 2 and 3. Alternatively, the blade 100 can be connected to the blade holder 200 through insert molding, such that the blade holder 200 is formed around the blade 100 during the manufacturing process.

The blade holder 200 further comprises, at a proximal end, a holder knob 215 vertically extending from the front face of the blade holder 200. The surface of holder knob 215 can include ridges 220 for increased traction when in contact with a finger during use of the safety scalpel 10. As described more fully below, the holder knob 215 is adapted to move the blade 100 between a closed and open position when in communication with the blade guard 300.

Figure 4:
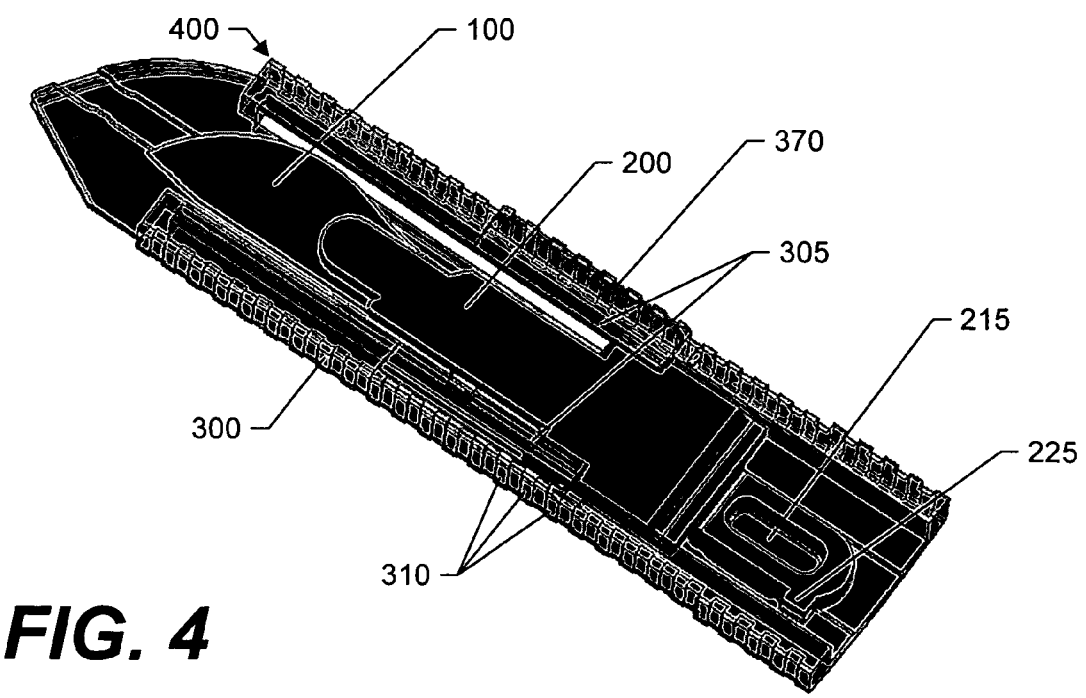
FIG. 4 illustrates a perspective view of a blade guard engaging the blade and blade holder in accordance with preferred embodiments of the present invention.
Figure 5:
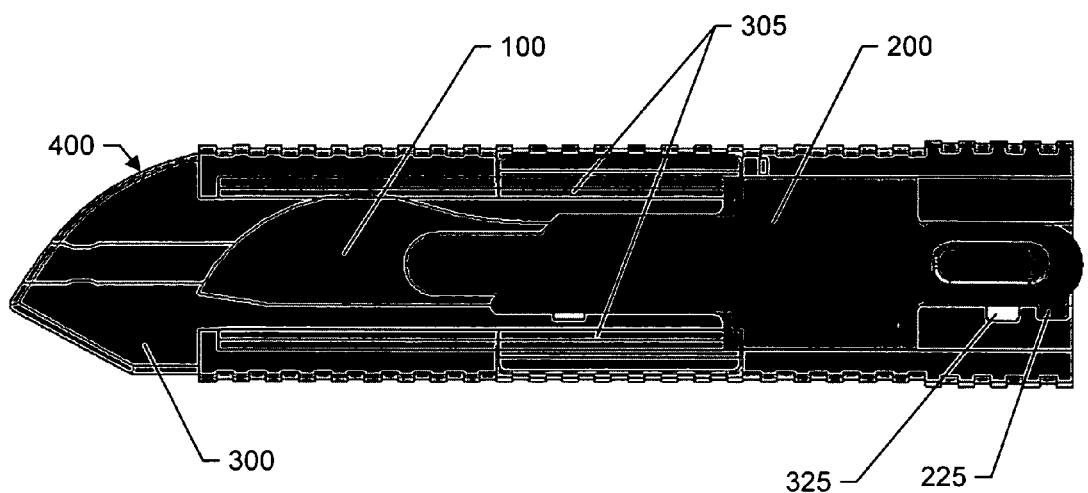
FIG. 5 illustrates a bottom view of the blade guard engaging the blade and blade holder, such that the blade holder is slideably received within the blade guard in accordance with preferred embodiments of the present invention.
Figure 6:
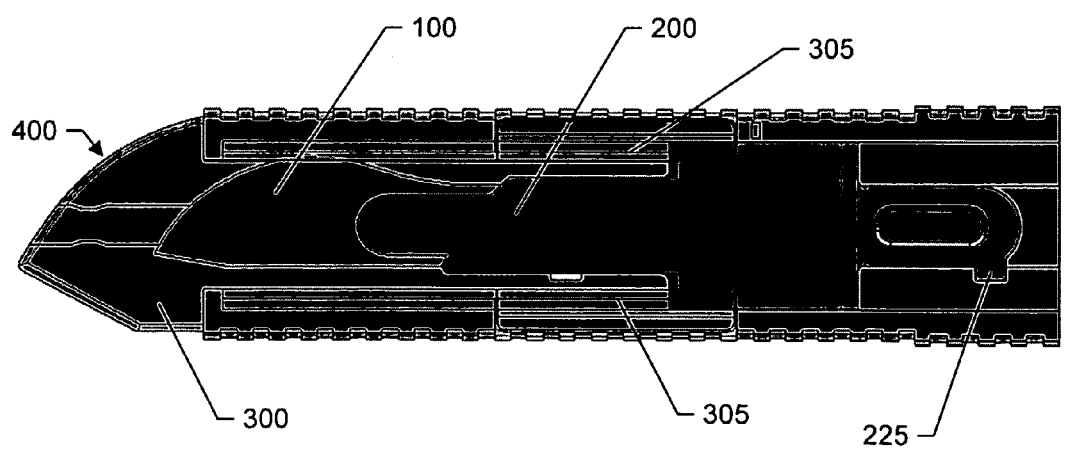
FIG. 6 illustrates a bottom view of the blade guard engaging the blade and blade holder, such that a portion of the blade holder is received by a rear retaining slot in accordance with preferred embodiments of the present invention.

As illustrated in FIGS. 4-6, blade guard 300 is designed to slideably receive the blade 100 and blade holder 200. When the blade 100 is in the closed position, the blade guard 300 adequately surrounds the blade 100, so that the blade 100 cannot inadvertently cut, puncture, or otherwise damage materials or individuals.

Figure 7:
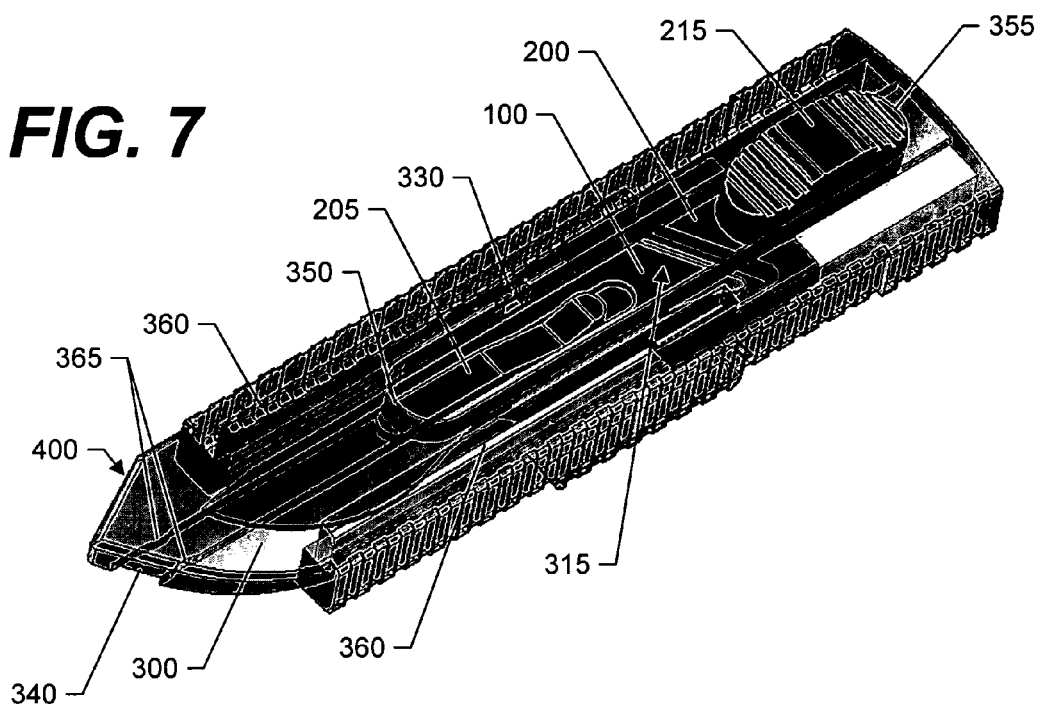
FIG. 7 illustrates a perspective view of the blade guard engaging the blade and blade holder, wherein the blade holder is in a closed position in accordance with preferred embodiments of the present invention.

The blade guard 300 comprises an aperture 315 (also referred to herein as slot 315), see FIG. 7, for providing a track for the holder knob 215 of the blade holder 200 to slide between the closed and open positions. Consequently, as the holder knob 215 moves between the closed and open positions, the blade holder 200 and the blade 100 also move between the closed and open positions. More particularly, a directional force applied to the holder knob 215 of the blade holder 200 permits the holder knob 215 to slide along the slot 315 when moving the blade 100 and blade holder 200 between the closed and open positions.

The blade guard 300 also comprises at least one lateral rail 305, such that the at least one lateral rail 305 defines a cavity within the blade guard 300. The blade 100 and blade holder 200 are positioned between preferably two lateral rails 305, such that the blade 100 and blade holder 200 slide within the cavity when the holder knob 215 slides within the slot 315. The holder knob 215 is positioned near a proximal end of the slot 315 when the blade 100 is in the closed position and the holder knob 215 is positioned near a distal end of the slot 315 when the blade 100 is in the open position.

As further illustrated in FIG. 7, the blade guard 300 comprises a forward catch 350 and rear catch 355, such that the forward catch 350 is positioned near the distal end of the slot 315 and the rear catch 355 is positioned near the proximal end of the slot 315. The forward catch 350 is adapted to engage the holder knob 215 when the blade 100 is in the open position. The forward catch 350 prevents the blade holder 200 from moving the blade 100 forwardly beyond the open position. Similarly, the rear catch 355 is adapted to engage the holder knob 215 when the blade 100 is in the closed position. The rear catch 355 prevents the blade holder 200 from moving the blade 100 rearwardly beyond the closed position. Alternatively, rear catch 355 prevents the blade holder 200 from moving the blade 100 rearwardly beyond the fully locked position.

For the safety scalpel 10 to be effectively used and safely stored, the blade 100 can be temporarily locked in the closed and open positions. To facilitate the temporary locking of the blade 100 in the closed position, the blade holder 200 further comprises a stopper rib 225, see FIGS. 5 and 6, positioned near the holder knob 215. Generally, the stopper rib 225 laterally extends from the front face of the blade holder 200.

The stopper rib 225 is adapted to engage a rear retaining slot 325 of the blade guard 300. The rear retaining slot 325 is located near the proximal end of the blade guard 300, such that the stopper rib 225 engages the rear retaining slot 325 when the blade 100 is in the closed position. During the engagement of the stopper rib 225 and the rear retaining slot 325, the blade 100 is temporarily maintained in the closed position.

To facilitate the temporary locking of the blade 100 in the open position, the blade guard 300 further comprises a front retaining slot 330 positioned near the distal end of the blade guard 300. The stopper rib 225 of the blade holder 200 engages the front retaining slot 330 when the blade 100 is in the open position. During the engagement of the stopper rib 225 and the front retaining slot 330, the blade 100 is temporarily maintained in the open position.

Alternatively, to further ensure that the blade 100 is adequately locked in the open position during use of the safety scalpel 10, the blade holder 200 can include a boss 230 generally positioned on the top of the holder protrusion 205. As illustrated in FIGS. 9B and 13B, the boss 230 of the blade holder 200 is configured to engage (by interference fit) a front slot 340 of the blade guard 300. The front slot 340 is positioned on a bottom face of the blade guard 300 near the distal end of the blade guard 300. When the blade 100 is moved to the open position, the boss 230 of the blade holder 200 snaps into the front slot 340 of the blade guard 300, such that the blade 100 is prevented from moving laterally or transversally during use.

Figure 15:
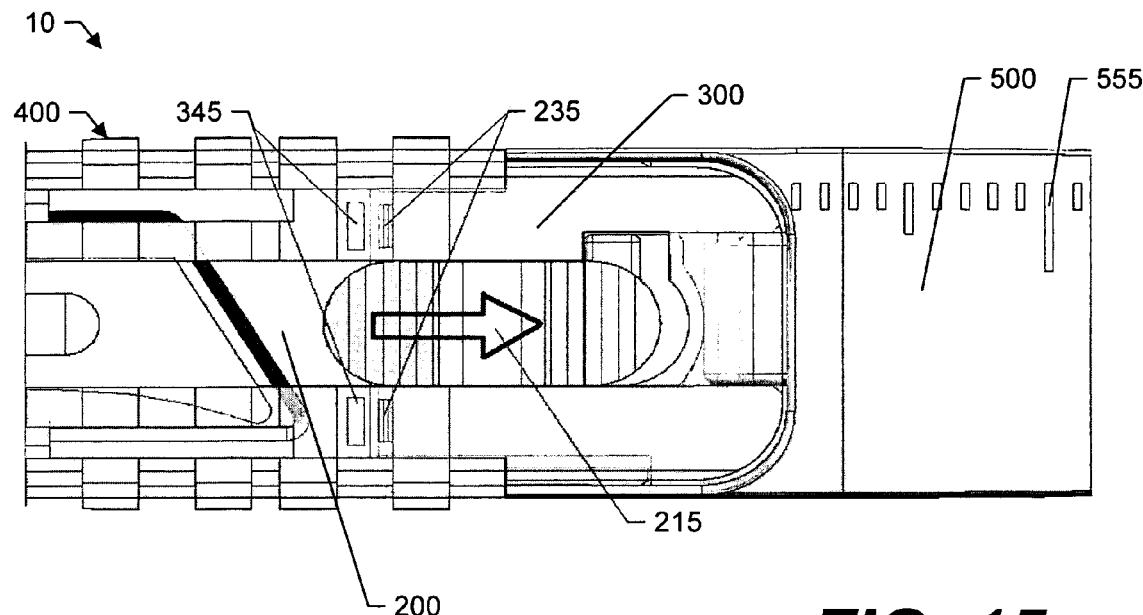
FIG. 15 illustrates a perspective view of the blade and blade holder in the closed position in accordance with an alternative embodiment of the present invention.
Figure 16:
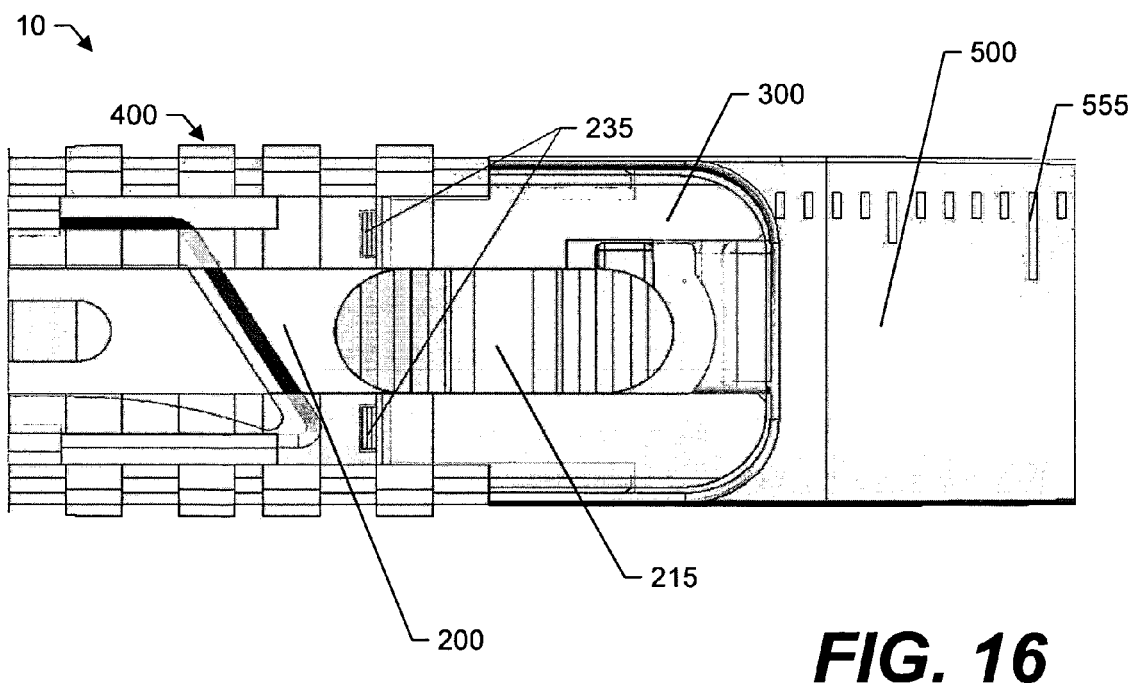
FIG. 16 illustrates a perspective view of the blade and blade holder in a fully locked position in accordance with an alternative embodiment of the present invention.

In another alternative embodiment of the present invention, the blade 100 can be locked into a fully-locked position, prior to dismounting the blade cartridge 400 from the scalpel handle 500 or after surgery has been completed. As illustrated in FIGS. 15 and 16, the blade holder 200 includes at least one locking slot 235 positioned near the proximal end of the blade holder 200. The at least one locking slot 235 can snap into at least one locking rib 345 of the blade guard 300 (located near the proximal end of the blade guard 300), thereby moving the blade 100 to a fully locked position. When the locking slot 235 engages the locking rib 345, the blade holder 200 is prevented from moving the blade 100 between the closed and open position.

Moreover, when the blade 100 is moved to the locked position, the blade 100 can no longer be released and extended forward to the open position for re-use. Typically, a rearwardly directional force is applied to the holder knob 215 of the blade holder 200, such that the blade 100 is moved beyond the closed position to the locked position.

Figure 9A:
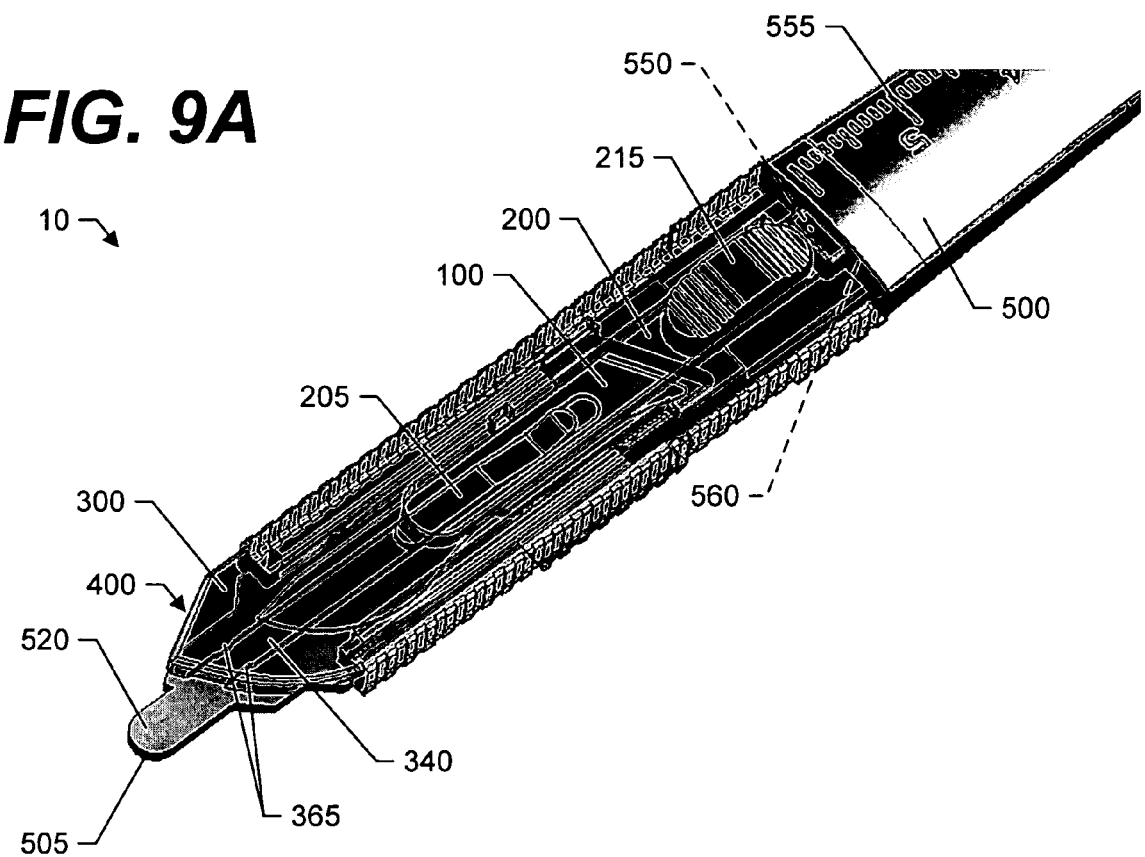
FIGS. 9A-9B, collectively referred to as FIG. 9, illustrate perspective views of the blade cartridge received by the distal end of the scalpel handle, such that support ribs of the scalpel handle secure the blade cartridge on the scalpel handle in accordance with preferred embodiments of the present invention.
Figure 9B:
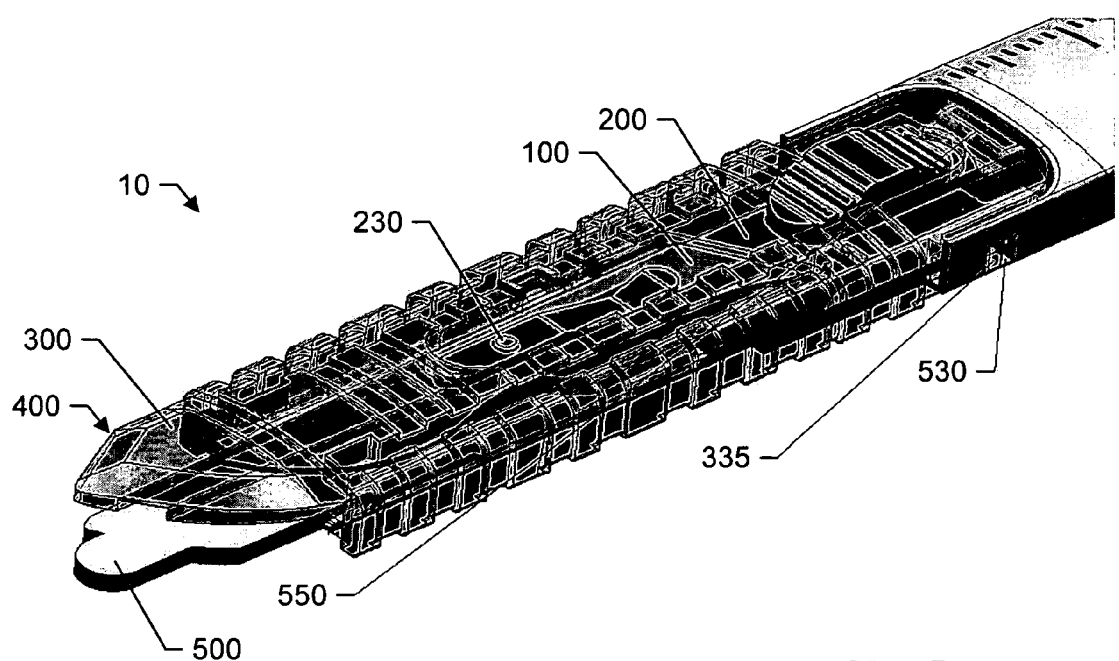
Figure 13A:
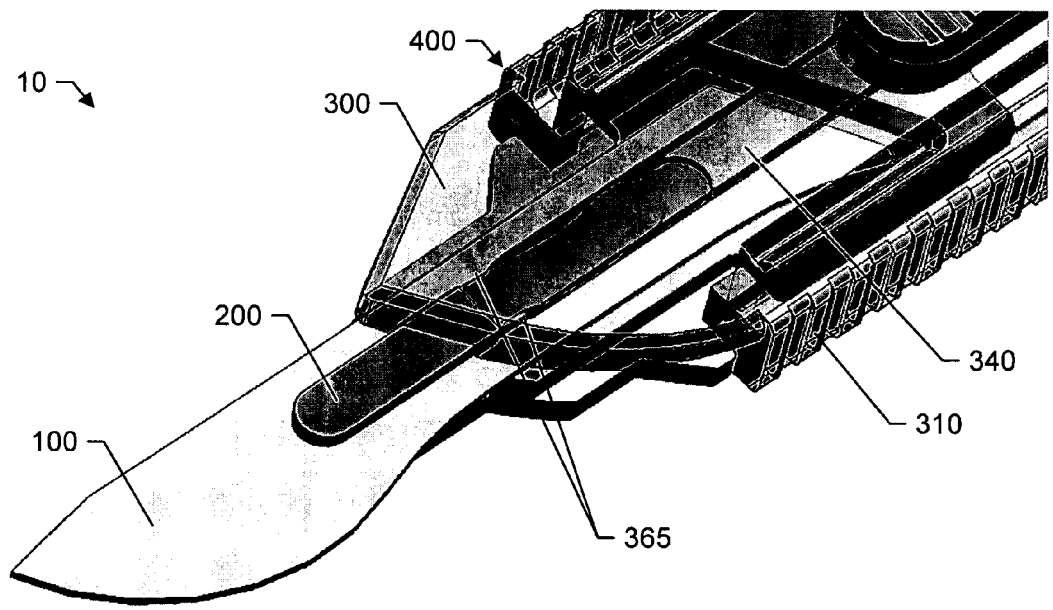
FIGS. 13A-13B, collectively referred to as FIG. 13, illustrate perspective views of the blade and blade holder of the blade cartridge in the open position, such that the blade is prevented from lateral and transverse movement in accordance with preferred embodiments of the present invention.
Figure 13B:
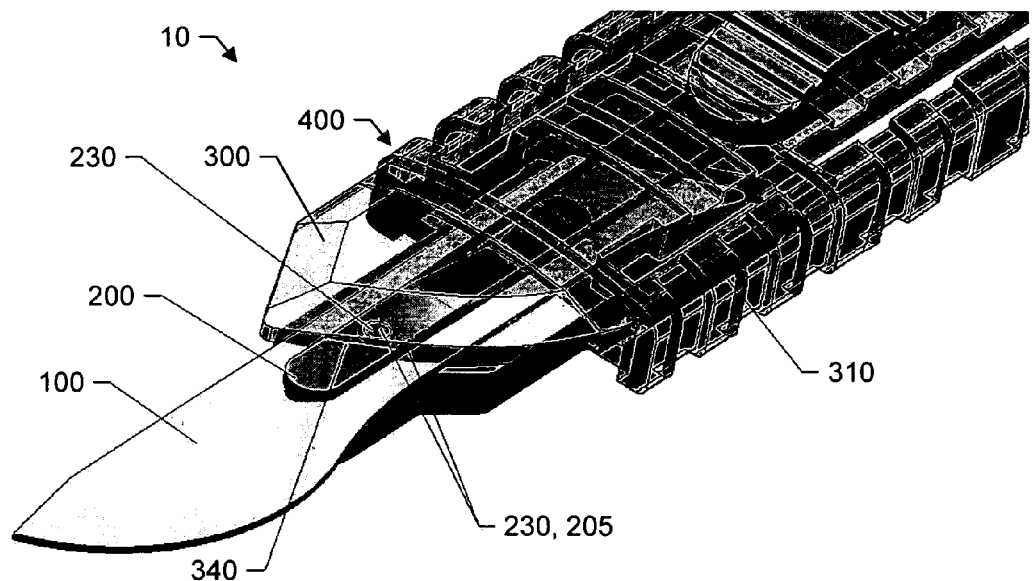

In a preferred embodiment, the blade guard 300 further comprises a plurality of tabs 365, see FIGS. 7, 9A, and 13A, positioned within the front slot 340. As the holder protrusion 205 of the blade holder 200 slides within front slot 340 when moved into the open position, the plurality of tabs 365 engage (by interference fit) the holder protrusion 205, such that the blade 100 is prevented from moving in a lateral or transverse direction.

One skilled in the art will recognize that the blade holder 200 and blade guard 300 can be made of a variety of materials including, but not limited to, plastic, such as acrylonitrile-butadiene-styrene (ABS) copolymer plastic.

As described above, the blade 100 and blade holder 200 fit into the blade guard 300. Collectively, these three elements form the blade cartridge 400. The blade cartridge 400 is attachable to and detachable from a distal end of the scalpel handle 500.

Figure 8A:
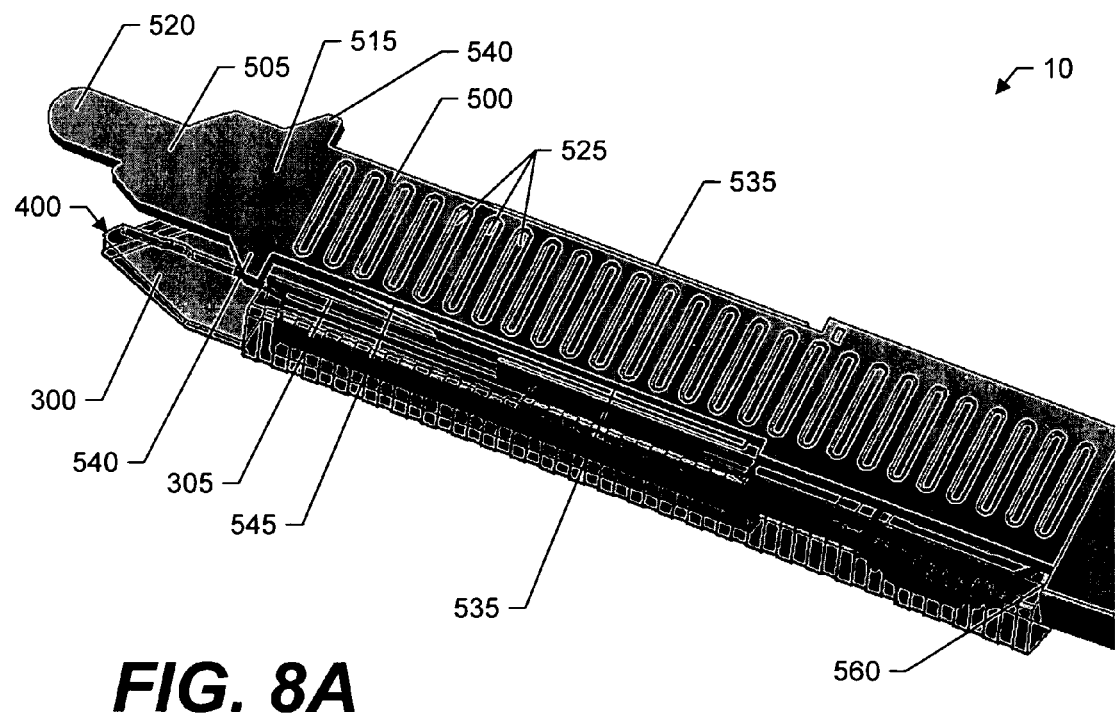
FIGS. 8A-8C, collectively referred to as FIG. 8, illustrate bottom views of the blade cartridge received by a distal end of a scalpel handle in accordance with preferred embodiments of the present invention.
Figure 8B:
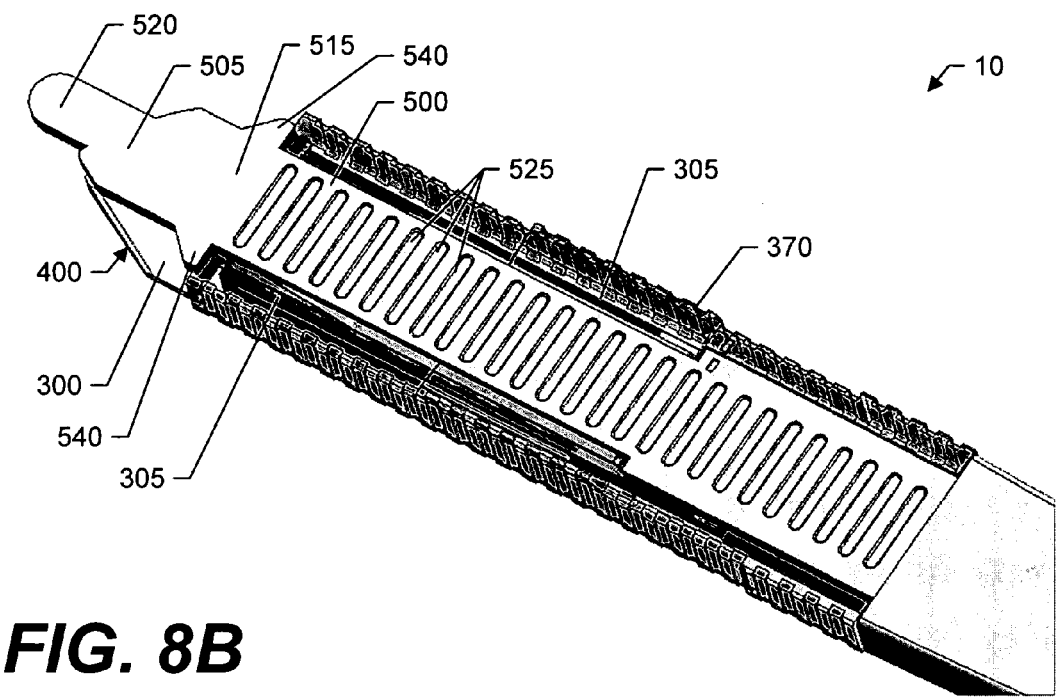
Figure 8C:
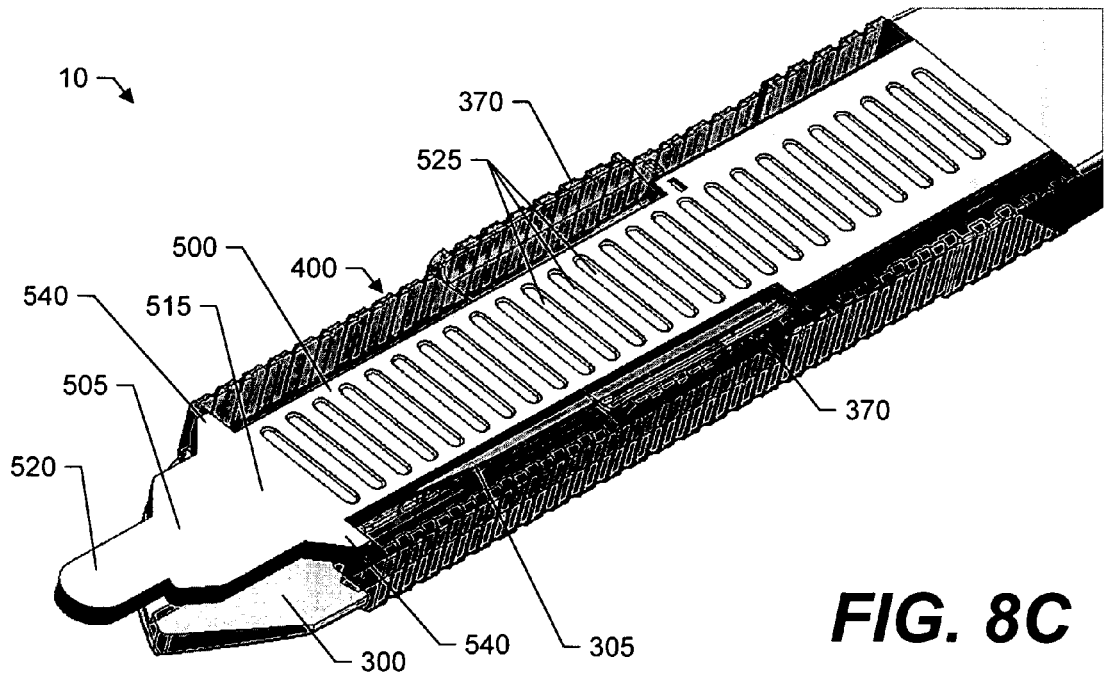

The distal end 505 of the scalpel handle 500 is cut on the front face 510 to accommodate the blade cartridge 400. The scalpel handle 500, as illustrated in FIGS. 8A-8C, comprises at least one lateral extension 540, a lower wall 560, a lower protrusion 550, and, alternatively, at least one medial notch 530 (see FIG. 9B). Preferably, two lateral extensions 540 are positioned near a distal end 505 of the scalpel handle 500, such that the first lateral extension 540 extends in a direction opposite the second lateral extension 540. Accordingly, the first lateral extension 540, the second lateral extension 540, and the scalpel handle 500 from a generally T-shape. The lateral extensions 540 are adapted to engage a distal end of the blade cartridge 400, when the blade cartridge 400 is attached to the scalpel handle 500.

The lower wall 560, as shown in FIG. 9A, communicates with a proximal end of the blade cartridge 400, when the blade cartridge 400 is attached to the scalpel handle 500. Generally, the distance between the lateral extensions 540 and the lower wall 560 of the scalpel handle 500 is generally equal to the length of the blade cartridge 400. Together, the lateral extensions 540 and lower wall 560 prevent longitudinal movement of the blade cartridge 400 when attached to the scalpel handle 500.

The lower protrusion 550 is positioned on the front face 510 of the scalpel handle 500 and extends longitudinally from the lower wall 560. Typically, the blade cartridge 400 is seated onto the lower protrusion 550 during attachment to the scalpel handle 500.

Figure 14:
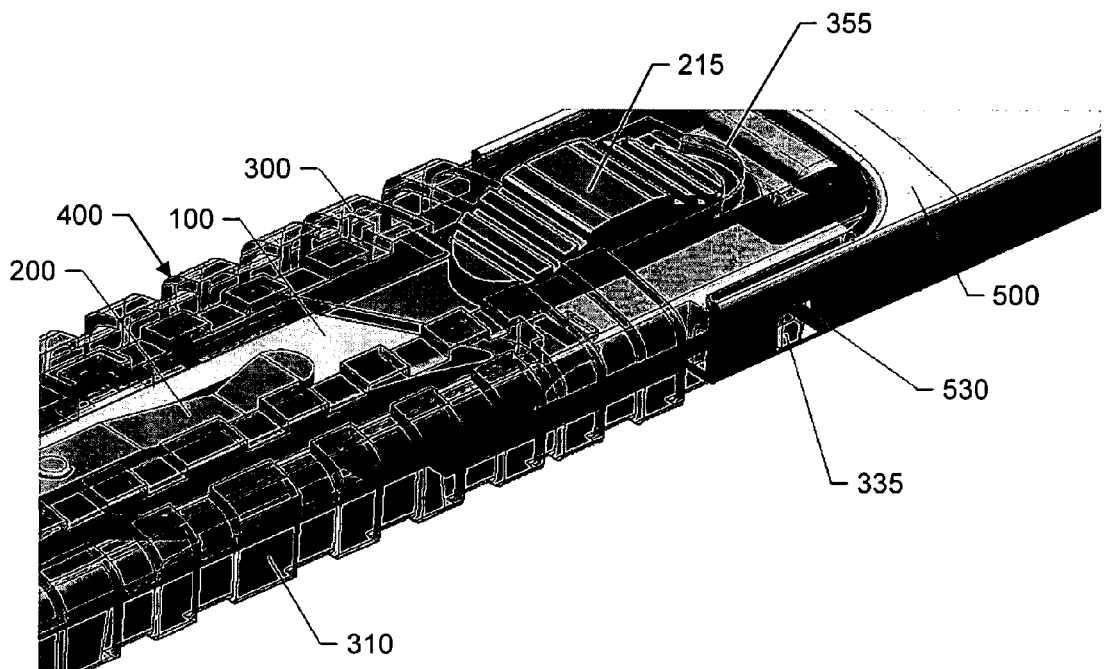
FIG. 14 illustrates a perspective view of the blade cartridge engaging with the distal end of the scalpel handle in accordance with an alternative embodiment of the present invention.

Alternatively, as illustrated in FIGS. 9B and 14, the at least one medial notch 530 is adapted to engage at least one catch 335 of the blade cartridge 400 (e.g., catch 335 of the blade guard 300). When the blade cartridge 400 is attached to the scalpel handle 500, the catch 335 of the blade cartridge 400 snaps into the notch 530 to prevent longitudinal movement of the blade cartridge 400.

In another embodiment, the lateral edges of the blade guard 300 include slanted ends at the proximal end of the blade cartridge 400. The slanted ends of the blade guard 300 engage the lower wall 560 of the scalpel handle 500 and are adapted to prevent longitudinal movement of the blade cartridge 400 during use of the safety scalpel 10.

For proper attachment of the blade cartridge 400 to the scalpel handle 500, the scalpel handle 500 further comprises at least one support rib 535. Preferably, two support ribs 535 are positioned on each lateral side of the distal end 505 of the scalpel handle 500. The blade cartridge 400 includes at least one rail 305 adapted to engage a support rib 535 of the scalpel handle 500. The engagement of the rail 305 and the support rib 535 temporarily maintains the attachment of the blade cartridge 400 to the distal end 505 of the scalpel handle 500.

As illustrated in FIG. 8A, the scalpel handle 500 further comprises a tapered portion 545 positioned near the lateral extensions 540. The tapered portion 545 of the scalpel handle 500 assists in the attachment and detachment of the blade cartridge 400 to the scalpel handle 500. Consequently, the tapered portion 545 of the scalpel handle 500 causes the support ribs 535 of the scalpel handle 500 to slightly taper. Because the scalpel handle 500 includes a tapered portion 545, only a portion of the lateral rails 305 of the blade cartridge 400 need to overcome the support ribs 535 of the scalpel handle 500 during attachment to and detachment from the scalpel handle 500.

For increased traction of the scalpel handle 500 when in contact with a finger during use of the safety scalpel 10, the scalpel handle 500 includes a plurality of grooves 525 positioned on a back face 515 of the scalpel handle 500. As illustrated in FIG. 8, the plurality of grooves 525 are positioned on the distal end 505 of the scalpel handle 500, such that the plurality of grooves 525 prevent slippage of the safety scalpel 10 during use.

Figure 10:
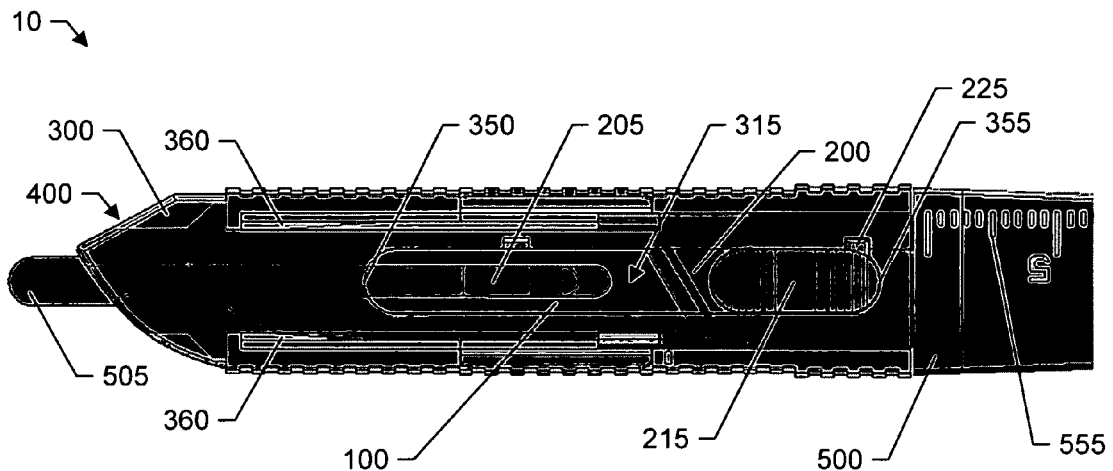
FIG. 10 illustrates a top view of the blade cartridge received by the distal end of the scalpel handle, such that the blade is wholly enclosed by the blade guard when the blade holder is in the closed position in accordance with preferred embodiments of the present invention.

As illustrated in FIGS. 1, 9, and 10, the scalpel handle 500 can include indicia 555. The indicia 555 are generally located on the front face 510 and near the proximal end 507 of the scalpel handle 500. While one skilled in the art will recognize that the indicia 555 of the present invention can include multiple markings or printings, the indicia 555 are preferably units of measurement such as, but not limited to, the metric system, the Imperial system, or any other appropriate measuring system.

The scalpel handle 500 is designed to accept the blade cartridge 400, and provide the user with the feel of a conventional scalpel when used. It is thus provided of materials, weight, and design for comfortable use by the user.

Assembly of Cartridge

The blade cartridge 400 includes the fitted cooperation of the blade 100, the blade holder 200 and the blade guard 300, as shown in FIG. 1. Preferably, the blade cartridge 400 is assembled offsite from where the present safety scalpel 10 is ultimately used, for example, in a factory, such that only the assembled blade cartridge 400 is delivered to the user. Also, as described above, the blade 100 can be attached to the blade holder 200 through insert molding, wherein the blade holder 200 is actually formed and molded around the blade 100. With the use of insert molding, the blade 100 need not be subsequently attached to the blade holder 200.

The blade cartridge 400 can be delivered in its own sterilized wrapping such as, for example, a foil wrap. Thus, the blade cartridge 400 is not intended for the user to assemble, but is intended only for the mating of the blade cartridge 400 with the scalpel handle 500.

As described above, the blade 100 is fixed to the blade holder 200 by aligning the blade aperture 120 with the corresponding holder protrusion 205 of the blade holder 200. The protrusion notch 210 permits the blade 100 to slide, slot, and snap onto the blade holder 200, as shown in FIGS. 2 and 3.

The blade holder 200 with the blade 100 is then attached to the blade guard 300 by sliding and slotting the blade holder 200 onto the first rail 305 of the blade guard 300. The lateral rails 305 of the blade guard 300 do not run the full length of the blade guard 300 and, therefore, the cavity within the blade guard 300 is wider near the proximal end of the blade guard 300. Such a wider cavity assists in the insertion of the blade 100 and blade holder 200 into the blade guard 300. To attach the blade 100 and blade holder 200 into the blade guard 300, the blade 100 and blade holder 200 are pushed into the blade guard 300, so that the blade 100 is aligned within the cavity defined by the lateral sides of the blade guard 300 and the holder knob 215 fits into slot 315. As illustrated in FIGS. 4-6, the blade holder 200 is slotted onto the blade guard 300 such that the stopper rib 225 on the blade holder 200 engages the rear retaining slot 325 of the blade guard 300.

The blade holder 200 and the blade 100 are kept temporarily locked in the blade guard 300 by the holder stopper rib 225 engaging and locking to the matching rear retaining slot 325 on the blade guard 300. Accordingly, the blade 100 can be kept in the closed position.

Figure 11:
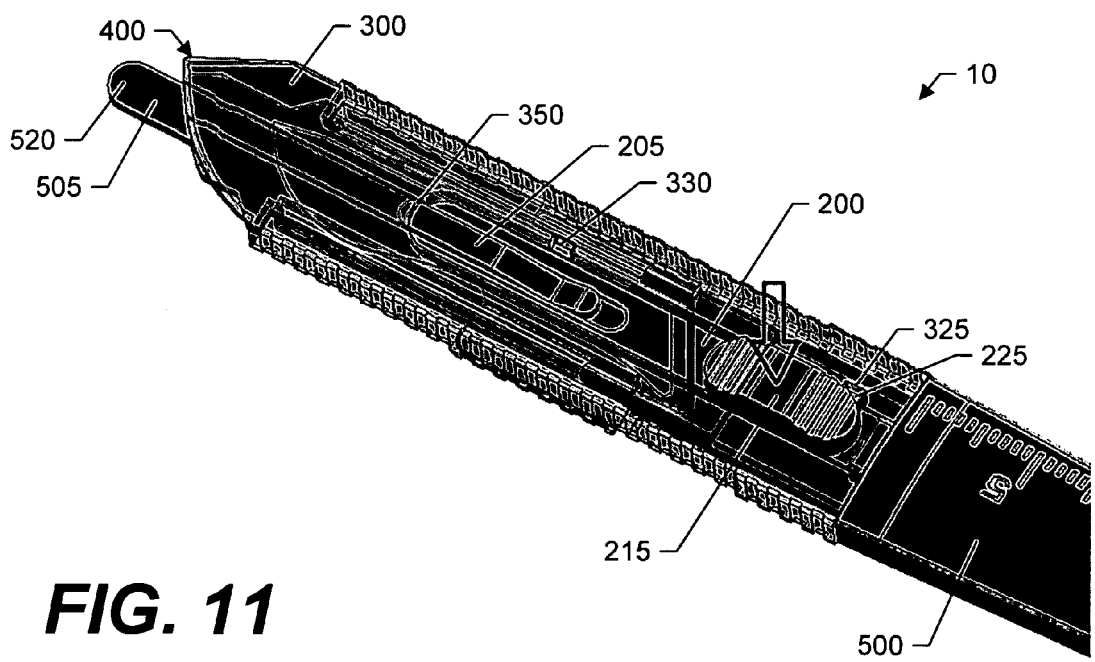
FIG. 11 illustrates a perspective view of the blade cartridge received by the distal end of the scalpel handle, wherein the blade cartridge includes a slot for allowing a holder knob to slide between the closed position and an open position in accordance with preferred embodiments of the present invention.
Figure 12:
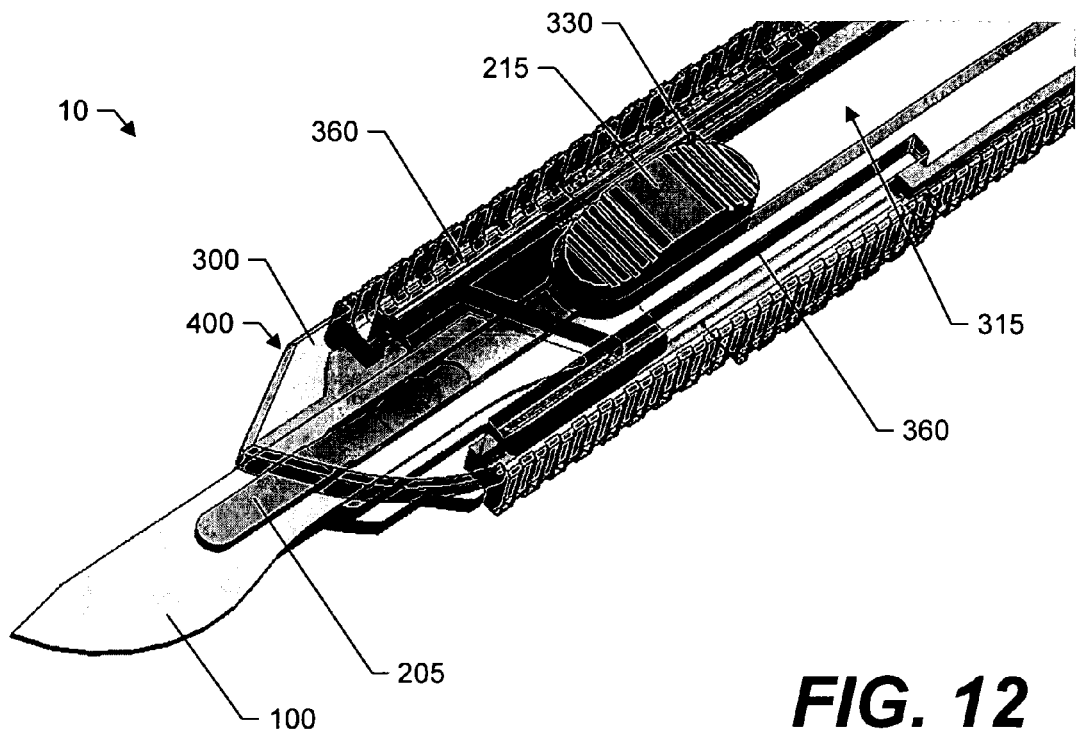
FIG. 12 illustrates a perspective view of the blade cartridge received by the distal end of the scalpel handle, such that the blade and blade holder are in the open position in accordance with preferred embodiments of the present invention.

In the assembled blade cartridge 400, the blade 100 is wholly enclosed in the blade guard 300 until mounted on the scalpel handle 500 for use. As illustrated in FIG. 11, to disengage the blade 100 from the closed position, the user needs to depress the holder knob 215, and then push the holder knob 215 forward. Accidental release of the blade 100 is thus prevented.

Mounting of Cartridge

To attach the blade cartridge 400 to the scalpel handle 500, the blade cartridge 400 must approach the scalpel handle 500 in a direction generally perpendicular to a longitudinal axis X of the scalpel handle 500. Generally, the blade cartridge 400 is attached to the scalpel handle 500 between the lateral extensions 540 and the lower wall 560.

Holding the blade cartridge 400 in one hand, the user positions a first inner edge of the blade cartridge 400 (e.g., a first rail 305 of the blade cartridge 400) onto a first outer edge of the scalpel handle 500 (e.g., a first support rib 535). The user then rotates the blade cartridge 400 in a direction generally perpendicular to the longitudinal axis X of the scalpel handle 500, such that a second inner edge of the blade cartridge 400 (e.g., a second rail 305 of the blade cartridge 400) approaches a second outer edge of the scalpel handle 500 (e.g., a second support rib 535). The second inner edge 305 of the blade cartridge 400 snaps, clicks, and engages the second support rib 535 of the scalpel handle 500.

Alternatively, the catches 335 of the blade cartridge 400 snap, click, and engage the medial notches 530 of the scalpel handle 500. Thus, the blade cartridge 400 is secured snugly to the scalpel handle 500.

As illustrated in FIGS. 9A-9B, longitudinal movements of the blade guard 300 are limited, and preferably prevented by the lateral extensions 540 and the lower wall 560 of the scalpel handle 500.

Further, as illustrated in FIGS. 7 and 10, the blade cartridge 400 (e.g., the blade guard 300) includes at least one groove 360 positioned near one lateral side of the blade cartridge 400. Preferably, two grooves 360 each positioned at opposite lateral sides of the blade cartridge 400 provide increased flexibility of the blade cartridge 400 during detachment from the scalpel handle 500. The grooves 360 of the blade cartridge 400 allow the lateral sides of the blade cartridge 400 to flex upwardly during the detachment of the blade cartridge 400 from the scalpel handle 500.

Use of Safety Scalpel

When first mounted, the blade 100 in the blade cartridge 400 is in the closed position, as illustrated in FIG. 10. The blade 100 is extended out of the blade guard 300 by depressing the holder knob 215 of the blade holder 200 (e.g, pushing the holder knob 215 downward); releasing the stopper rib 225 on the blade holder 200 from the rear retaining slot 325 on the blade guard 300; sliding the holder knob 215 along the slot 315 of the blade guard 300 until the blade 100 reaches the open position, upon which the holder knob 215 is released such that the stopper rib 225 on the blade holder 200 engages the front retaining slot 330 on the blade guard 300. Thus, the blade 100 is temporarily locked in the open position.

The blade 100 and blade holder 200 are secured within slot 340, when in the open position, by interference fit of the tabs 365 and the holder protrusion 205, as illustrated in FIGS. 7 and 9A. In this open position, the safety scalpel 10 is ready for use. The interference fit between the tabs 365 and the holder protrusion 205 prevent the blade 100 from moving laterally and transversally during use of the safety scalpel 10.

Alternatively, the blade 100 and blade holder 200 are further secured to the blade guard 300 by interference fits of the boss 230 on blade holder 200 and the front slot 340 on the blade guard 300, as illustrated in FIGS. 9B and 13B. The interference fit between the boss 230 and the front slot 340 prevent the blade 100 from moving laterally and transversally during use of the safety scalpel 10.

The blade cartridge 400 (e.g., the blade guard 300) further comprises a plurality of indentations 310, as illustrated in FIGS. 4, 13 and 14. The plurality of indentations 310 are positioned on at least one lateral side of the blade guard 300, such that the plurality of indentions 310 provide increased grip of the safety scalpel 10 during use.

If the surgeon needs to hand the safety scalpel 10 to a colleague, she first moves the blade 100 into the closed position by depressing the holder knob 215 on the blade holder 200 to release the stopper rib 225 from the front retaining slot 330; sliding the holder knob 215 back along the slot 315 of the blade guard 300, until the blade 100 reaches the closed position, upon which the holder knob 215 is released such that the stopper rib 225 on the blade holder 200 re-engages the rear retaining slot 325 on the blade guard 300. The blade 100 is now temporarily locked in the closed position. The blade 100 can be moved any number of times between the open and closed positions until the operation is completed.

Dismounting of Cartridge

To detach the blade cartridge 400 from the scalpel handle 500, the blade cartridge 400 must be removed from the scalpel handle 500 in a direction generally perpendicular to the longitudinal axis X of the scalpel handle 500. Accordingly, a user cannot push the blade cartridge 400 off of the scalpel handle 500 in a longitudinal direction, because of the lateral extensions 540. If it were possible to remove the blade cartridge 400 from the scalpel handle 500 in a longitudinal direction, one can accidentally project or propel the blade cartridge 400 towards an open incision previously created by the safety scalpel 10, or in another undesirable direction or location. The present invention eliminates this possibility.

Removal of the blade cartridge 400 occurs after the blade 100 has been moved to the closed or fully locked position. To remove the blade cartridge 400 from the scalpel handle 500, the user slightly disengages one edge of the blade cartridge 400 (e.g., a first rail 205 of the blade cartridge 400) from the corresponding outer edge of the scalpel handle 500 (e.g., a support rib 535). The user then rotates the blade cartridge 400 in a direction generally perpendicular the longitudinal axis X of the scalpel handle 500. Such a rotation will fully disengage a first edge of the blade cartridge 400 (e.g., a first rail 205 of the blade cartridge 400) from the outer edge of the scalpel handle 500 (e.g., a first support rib 535). The used blade cartridge 400 is then disposed of safely.

In an alternative embodiment, the blade cartridge 400 further provides at least one ridge 370 positioned on at least one lateral side of the blade guard 300, as illustrated in FIGS. 4, 8B, and 8C. The at least one ridge 370 of the blade cartridge 400 provides increased traction and support for the user during detachment of the blade cartridge 400 from the scalpel handle 500. The user can apply a finger to the at least one ridge 370 to assist in disengaging a first edge of the blade cartridge 400 with a first outer edge of the scalpel handle 500.

Further, as illustrated in FIGS. 7 and 10, the two grooves 360 positioned at opposite lateral sides of the blade cartridge 400 provide increased flexibility of the blade cartridge 400 during detachment from the scalpel handle 500. The grooves 360 of the blade cartridge 400 allow the lateral sides of the blade cartridge 400 to flex upwardly during the detachment of the blade cartridge 400 from the scalpel handle 500.

Disposable Safety Scalpel

In still another alternative embodiment of the present invention, the safety scalpel 10 comprises a disposable scalpel handle 500, such that the disposable scalpel handle 500 is separate and passive from the blade cartridge 400. The disposable scalpel handle 500 is adapted to attach to the blade cartridge 400. Preferably, the blade cartridge 400 and the disposable scalpel handle 500 are permanently fixed to each other at the factory during the manufacturing process of the safety scalpel 10. After use, the blade cartridge 400 and disposable scalpel handle 500 are properly discarded.

One skilled in the art will recognize that the disposable scalpel handle 500 can be made of a variety of materials including, but not limited to, plastic, such as acrylonitrile-butadiene-styrene (ABS) copolymer plastic.

In yet another alternative embodiment of the present invention, the safety scalpel 10 comprises a disposable scalpel handle 500 having a slideable blade 100 and blade holder 200 received therein. Accordingly, the blade guard 300 is an integral part of the disposable scalpel handle 500 and, therefore, does not detach from the scalpel handle 500. Further, the entire safety scalpel 10 is disposable after use.

The blade 100 and blade holder 200 can be attached as described above, by aligning the aperture 120 of the blade 100 with the holder protrusion 205 of the blade holder 200. Alternatively, the blade 100 and blade holder 200 can be attached through insert molding, such that the blade holder 200 is formed around the blade 100 during the manufacturing process.

At a proximal end, the blade holder 200 further comprises a holder knob 215 vertically extending from the front face of the blade holder 200. The surface of the holder knob 215 can include ridges 220 for increased traction when in contact with a finger during use of the safety scalpel 10.

The blade guard 300 is integral to the disposable scalpel handle 500 and defines a cavity that slideably receives the blade 100 and blade holder 200. When in the closed position, the blade guard 200 completely surrounds the blade 100, but in the open position, a portion of the blade 100 extends outside the blade guard 300.

The blade guard 300 further comprises an aperture 315 (or slot 315) that provides a track for the holder knob 215 to slide between the closed and open positions. As described above, the holder knob 215 is positioned near a proximal end of the slot 315 when the blade 100 is in the closed position and the holder knob 215 is positioned near a distal end of the slot 315 when the blade 100 is in the open position.

The blade guard 300 comprises a forward catch 350 and rear catch 355, such that the forward catch 350 is positioned near the distal end of the slot 315 and the rear catch 355 is positioned near the proximal end of the slot 315. The forward catch 350 is adapted to engage the holder knob 215 when the blade 100 is in the open position. The forward catch 350 prevents the blade holder 200 from moving the blade 100 forwardly beyond the open position. Similarly, the rear catch 355 is adapted to engage the holder knob 215 when the blade 100 is in the closed position. The rear catch 355 prevents the blade holder 200 from moving the blade 100 rearwardly beyond the closed position. Alternatively, rear catch 355 prevents the blade holder 200 from moving the blade 100 rearwardly beyond the fully locked position.

For the safety scalpel 10 to be effectively used and safely stored, the blade 100 can be temporarily locked in the closed and open positions. To facilitate the temporary locking of the blade 100 in the closed position, the blade holder 200 further comprises a stopper rib 225, see FIGS. 5 and 6, positioned near the holder knob 215. Generally, the stopper rib 225 laterally extends from the front face of the blade holder 200.

The stopper rib 225 is adapted to engage a rear retaining slot 325 of the blade guard 300. The rear retaining slot 325 is located near the proximal end of the blade guard 300, such that the stopper rib 225 engages the rear retaining slot 325 when the blade 100 is in the closed position. During the engagement of the stopper rib 225 and the rear retaining slot 325, the blade 100 is temporarily maintained in the closed position.

To facilitate the temporary locking of the blade 100 in the open position, the blade guard 300 further comprises a front retaining slot 330 positioned near the distal end of the blade guard 300. The stopper rib 225 of the blade holder 200 engages the front retaining slot 330 when the blade 100 is in the open position. During the engagement of the stopper rib 225 and the front retaining slot 330, the blade 100 is temporarily maintained in the open position.

Alternatively, to further ensure that the blade 100 is adequately locked in the open position during use of the safety scalpel 10, the blade holder 200 can include a boss 230 generally positioned on the top of the holder protrusion 205. As illustrated in FIGS. 9B and 13B, the boss 230 of the blade holder 200 is configured to engage (by interference fit) a front slot 340 of the blade guard 300. The front slot 340 is positioned on a bottom face of the blade guard 300 near the distal end of the blade guard 300. When the blade 100 is moved to the open position, the boss 230 of the blade holder 200 snaps into the front slot 340 of the blade guard 300, such that the blade 100 is prevented from moving laterally or transversally during use.

Alternatively, the blade 100 can be locked into a fully-locked position, prior to discarding the safety scalpel 10 after surgery has been completed. As illustrated in FIGS. 15 and 16, the blade holder 200 includes at least one locking slot 235 positioned near the proximal end of the blade holder 200. The at least one locking slot 235 can snap into at least one locking rib 345 of the blade guard 300 (located near the proximal end of the blade guard 300), thereby moving the blade 100 in a fully locked position. When the locking slot 235 engages the locking rib 345, the blade holder 200 is prevented from moving the blade 100 between the closed and open position.

Moreover, when the blade 100 is moved to the locked position, the blade 100 can no longer be released and extended forward to the open position for re-use. Typically, a rearwardly directional force is applied to the holder knob 215 of the blade holder 200, such that the blade 100 is moved beyond the closed position to the locked position.

The blade guard 300 further comprises a plurality of tabs 365 positioned within the front slot 340. As the holder protrusion 205 of the blade holder 200 slides within front slot 340 when moved into the open position, the plurality of tabs 365 engage (by interference fit) the holder protrusion 205, such that the blade 100 is prevented from moving in a lateral or transverse direction.

For increased traction of the scalpel handle 500 when in contact with a finger during use of the safety scalpel 10, the scalpel handle 500 includes a plurality of grooves 525 positioned on a back face 515 of the scalpel handle 500. As illustrated in FIGS. 8A-8C, the plurality of grooves 525 are positioned on the distal end 505 of the scalpel handle 500, such that the plurality of grooves 525 prevent slippage of the safety scalpel 10 during use.

As illustrated in FIGS. 1, 9A, and 10, the scalpel handle 500 can include indicia 555. The indicia 555 are generally located on the front face 510 and near the proximal end 507 of the scalpel handle 500. While one skilled in the art will recognize that the indicia 555 of the present invention can include multiple markings or printings, the indicia 555 are preferably units of measurement such as, but not limited to, the metric system, the Imperial system, or any other appropriate measuring system.

The blade 100 is extended out of the blade guard 300 by depressing the holder knob 215 of the blade holder 200 (e.g, pushing the holder knob 215 downward); releasing the stopper rib 225 on the blade holder 200 from the rear retaining slot 325 on the blade guard 300; sliding the holder knob 215 along the slot 315 of the blade guard 300 until the blade 100 reaches the open position, upon which the holder knob 215 is released such that the stopper rib 225 on the blade holder 200 engages the front retaining slot 330 on the blade guard 300. Thus, the blade 100 is temporarily locked in the open position.

The blade 100 and blade holder 200 are secured within slot 340, when in the open position, by interference fit of the tabs 365 and the holder protrusion 205, as illustrated in FIGS. 7, 9A, and 13A. In this open position, the safety scalpel 10 is ready for use. The interference fit between the tabs 365 and the holder protrusion 205 prevent the blade 100 from moving laterally and transversally during use of the safety scalpel 10.

Alternatively, the blade 100 and blade holder 200 are further secured to the blade guard 300 by interference fits of the boss 230 on blade holder 200 and the front slot 340 on the blade guard 300, as illustrated in FIGS. 9B and 13B. The interference fit between the boss 230 and the front slot 340 prevent the blade 100 from moving laterally and transversally during use of the safety scalpel 10.

The blade guard 300 further comprises a plurality of indentations 310, as illustrated in FIGS. 4, 13A-B, and 14. The plurality of indentations 310 are positioned on at least one lateral side of the blade guard 300, such that the plurality of indentions 310 provide increased grip of the safety scalpel 10 during use.

If the surgeon needs to hand the safety scalpel 10 to a colleague, she first moves the blade 100 into the closed position by depressing the holder knob 215 on the blade holder 200 to release the stopper rib 225 from the front retaining slot 330; sliding the holder knob 215 back along the slot 315 of the blade guard 300, until the blade 100 reaches the closed position, upon which the holder knob 215 is released such that the stopper rib 225 on the blade holder 200 re-engages the rear retaining slot 325 on the blade guard 300. The blade 100 is now temporarily locked in the closed position. The blade 100 can be moved any number of times between the open and closed positions till the operation is completed.

Further, the blade guard 300 can comprise a plurality of knob tabs adapted to engage the holder knob 215 of the blade holder 200 when in the open and closed position. The interference fit of the holder knob 215 and the knob tabs prevents longitudinal movement of the holder knob 215 during use of the safety scalpel 10.

The blade guard 300 can further comprise a plurality of retaining slot tabs positioned in the front retaining slot 330, such that the retaining slot tabs are adapted to engage the stopper rib 225 when the blade 100 is in the open position. The interference fit between the retaining slot tabs and the stopper rib 225 prevents longitudinal movement of the blade 100 during use of the safety scalpel 10.

One skilled in the art will recognize that the scalpel handle 500 (e.g., the entire safety scalpel 10, minus the blade 100) can be made of a variety of materials including, but not limited to, plastic, such as acrylonitrile-butadiene-styrene (ABS) copolymer plastic.

While the invention has been disclosed in its preferred forms, it will be apparent to those skilled in the art that many modifications, additions, and deletions can be made therein without departing from the spirit and scope of the invention and its equivalents, as set forth in the following claims.

We claim:

1. A safety scalpel comprising:
   a reusable scalpel handle having a longitudinal axis;
   a disposable blade cartridge attachable to the reusable scalpel handle by a snap fit, the disposable blade cartridge having a blade, a blade holder in communication with the blade, and a blade guard adapted to receive the blade and blade holder;
   wherein the disposable blade cartridge is attached to the reusable scalpel handle by engaging the blade cartridge against an outer edge of the scalpel handle and rotating the blade cartridge about a rotational axis substantially parallel to the longitudinal axis of the scalpel handle to wrap the cartridge at least partially around a portion of the scalpel handle, the snap fit occurring during the rotation of the blade cartridge;
   the reusable scalpel handle comprising:
      at least one lateral extension adapted to engage a distal end of the blade cartridge; and
      a lower wall adapted to engage a proximal end of the blade cartridge;
      wherein the at least one lateral extension and lower wall prevent longitudinal movement of the blade cartridge when attached to the scalpel handle; and
      at least one support rib adapted to engage at least one rail of the disposable blade cartridge, wherein the engagement of the at least one support rib and the at least one rail temporarily maintains the attachment of the disposable blade cartridge onto the reusable scalpel handle.

2. The safety scalpel of claim 1, wherein the blade holder is adapted to move a portion of the blade between a closed position inside the blade guard and an open position outside the blade guard.

3. The safety scalpel of claim 1, wherein the blade is carbon steel.

4. The safety scalpel of claim 1, wherein the blade is stainless steel.

5. The safety scalpel of claim 1, wherein the blade holder is made of plastic.

6. The safety scalpel of claim 5, wherein the blade holder is made of acrylonitrile-butadiene-styrene (ABS) copolymer plastic.

7. The safety scalpel of claim 1, wherein the blade guard is made of plastic.

8. The safety scalpel of claim 7, wherein the blade guard is made of acrylonitrile-butadiene-styrene (ABS) copolymer plastic.

9. The safety scalpel of claim 1, wherein the handle comprises a plurality of grooves for preventing slippage of the handle during use.

10. The safety scalpel of claim 1, wherein the handle comprises a plurality of indicia.

11. The safety scalpel of claim 10, wherein the indicia are units of measurement.

12. The safety scalpel of claim 1, wherein the blade holder comprises a protrusion and the blade comprises an aperture adapted to receive the protrusion to secure the blade to the blade holder.

13. The safety scalpel of claim 1, wherein the blade is attached to the blade holder by insert molding.

14. The safety scalpel of claim 1, the blade holder further comprising a holder knob for moving the blade holder relative to the blade guard.

15. The safety scalpel of claim 14, the blade guard further comprising a forward catch and a rear catch, the forward and rear catches limiting movement of the holder knob.

16. The safety scalpel of claim 1, wherein the blade holder can be locked in an extended position with the blade exposed from within the blade guard.

17. The safety scalpel of claim 1, wherein the blade holder can be locked in a retracted position with the blade disposed entirely within the blade guard.

18. The safety scalpel of claim 1, the blade cartridge further comprising a groove for increasing flexibility of the blade cartridge during attachment to and detachment from the scalpel handle.

* * * * *